US011953496B2

(12) United States Patent
Tschampl et al.

(10) Patent No.: US 11,953,496 B2
(45) Date of Patent: Apr. 9, 2024

(54) CHEMISTRY/INSTRUMENT PARAMETER COLOR MAINTENANCE

(71) Applicant: Hach Company, Loveland, CO (US)

(72) Inventors: Michael Jonathan Tschampl, Windsor, CO (US); Peter Michalski, Broomfield, CO (US); Reece W. Hopkins, Charleston, SC (US); Frederik Nordahl, Glienicke (DE)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 17/621,024

(22) PCT Filed: Aug. 19, 2020

(86) PCT No.: PCT/US2020/046930
§ 371 (c)(1),
(2) Date: Dec. 20, 2021

(87) PCT Pub. No.: WO2021/034897
PCT Pub. Date: Feb. 25, 2021

(65) Prior Publication Data
US 2022/0334098 A1    Oct. 20, 2022

Related U.S. Application Data

(60) Provisional application No. 62/888,820, filed on Aug. 19, 2019.

(51) Int. Cl.
*G01N 33/487* (2006.01)
*B01L 3/00* (2006.01)

(52) U.S. Cl.
CPC ........ *G01N 33/48771* (2013.01); *B01L 3/545* (2013.01); *B01L 2200/16* (2013.01)

(58) Field of Classification Search
None
See application file for complete search history.

(56) References Cited

U.S. PATENT DOCUMENTS 4,904,605 A    2/1990  O'Brien et al.
5,597,532 A    1/1997  Connolly
(Continued)

FOREIGN PATENT DOCUMENTS

DE    102007000551 A1 *  4/2009  ............... G01D 1/14

OTHER PUBLICATIONS

International Search Report for PCT Application, PCT/US2020/046930, dated Dec. 9, 2020, 7 pages.

*Primary Examiner* — P. Kathryn Wright
(74) *Attorney, Agent, or Firm* — Ference & Associates LLC

(57) ABSTRACT

The invention provides a method for selecting a color for a chemistry or instrument based upon a parameter of a test, the method including: identifying a color corresponding to a parameter of a test for the parameter; selecting, if the color corresponding to the parameter has not previously been used for another parameter, the color for designating a chemistry or an instrument as corresponding to the parameter; selecting, if the color corresponding to the parameter has previously been used for another parameter, a different color other than the color for designating a chemistry or an instrument as corresponding to the parameter, wherein the selecting a color other than the color comprises identifying a color having a measure of change in visual perception of the different color against other previously selected colors a predetermined value from the other previously selected colors; and utilizing the selected colors for parameters across both chemistries (102, 104, 105) and instruments (101, 103) that are utilized in tests for the parameters.

6 Claims, 5 Drawing Sheets

(56) References Cited

U.S. PATENT DOCUMENTS

| | | |
|---|---|---|
| 2005/0176059 A1 | 8/2005 | Pal et al. |
| 2006/0177344 A1 | 8/2006 | Ouchi et al. |
| 2008/0003148 A1 | 1/2008 | Dause |
| 2016/0232421 A1 | 8/2016 | Decker et al. |
| 2019/0011419 A1 | 1/2019 | Sancoff et al. |
| 2020/0256844 A1* | 8/2020 | Majima ............... G01N 33/49 |

* cited by examiner

| Analyte | Code |
|---|---|
| XX Chloride | 7629 |
| Cl₂ Chlorine Total | 7626 |
| Cl₂ Chlorine Free | 708 |
| ClO₂ Chlorine Dioxide | 213 |
| XX pH | 7636 |
| XX Nitrogen | 7679 |
| NO₂ Nitrite | 254 |
| NO₂ Nitrate | 235 |
| CaMg Hardness High Range | 463 |
| CaMg Hardness Low Range | 465 |
| CaMg Hardness Low Low Range | 467 |
| XX Sulfate | 472 |
| XX Silica | 7613 |
| Cu Copper | 405 |
| Cu Copper | 403 |
| MoO³⁺ Molybdenum | 5753 |
| MoO₄ Molybdate | 5783 |
| Zn Zinc | 5497 |
| Mn Manganese High Range | 438 |
| Mn Manganese | 436 |
| Al Aluminum | 5145 |
| XX Low | Cool Gray 1c |
| XX Low | Black 6c |

| Analyte | Code |
|---|---|
| XX Phosporus | 302 |
| PO₄ Phosphate High Range | 300 |
| PO₄ Phosphate Low Range | 297 |
| O₂ Dissolved Oxygen | 311 |
| O₃ Ozone | 314 |
| XX Biochemical Oxygen Demand | 7475 |
| XX Chemical Oxygen Demand | 7716 |
| XX Oxygen Demand | 7472 |
| NH₃ Ammonia | 2411 |
| NH₃ Ammonia Free | 364 |
| NH₃ Ammonia | 360 |
| NH₄ Ammonium | 3415 |
| Alk Alkalinity High Range | 7747 |
| Alk Alkalinity Low Range | 7744 |
| XX Fluoride | 457 |
| Fe Iron | 7408 |
| NH₂Cl Monochloramine | 144 |
| Br Bromine | 7416 |

FIG. 2

CHEMISTRY/INSTRUMENT PARAMETER COLOR MAINTENANCE

FIELD

This application relates generally to maintaining consistency for parameter colors across a plurality of chemistries and instruments that are used in tests for those parameters.

BACKGROUND

Identifying a particular quality of different aqueous samples (e.g., testing for pH or chlorine content of a water source, etc.) is critical to ensuring safety for living creatures that may consume or reside in the water source from which the sample was taken, and for ensuring a healthy ecosystem. To determine the quality of these samples, a person can test for different parameters that assist in determining if the sample includes harmful elements, levels of elements that would indicate a low-quality sample, or the like. For example, high levels of lead within a water sample may indicate that the water is of low quality and may be harmful if consumed. The number of different parameters that can be tested for is large, with most parameters requiring the use of a different chemistry or test instrument for testing. For example, a user may test a water sample for pH, chlorine values, iron values, and the like, with each of these parameters utilizing a different chemistry and/or instrument for testing. Thus, a person who frequently tests for different parameters may carry or stock many different chemistries and/or instruments in order to perform these tests.

BRIEF SUMMARY

One embodiment provides a method for selecting a color for a chemistry or instrument based upon an parameter of a test, the method comprising: identifying a color corresponding to a parameter of a test for the parameter; selecting, if the color corresponding to the parameter has not previously been used for another parameter, the color for designating a chemistry or an instrument as corresponding to the parameter; selecting, if the color corresponding to the parameter has previously been used for another parameter, a different color other than the color for designating a chemistry or an instrument as corresponding to the parameter, wherein the selecting a color other than the color comprises identifying a color having a measure of change in visual perception of the different color against other previously selected colors a predetermined value from the other previously selected colors; and utilizing the selected colors for parameters across both chemistries and instruments that are utilized in tests for the parameters.

Another embodiment provides a method for maintaining a color for a parameter across chemistries and instruments that are used in tests for the parameter, the method comprising: identifying a parameter corresponding to the chemistry or the instrument, wherein the parameter comprises a parameter that the chemistry or the instrument is utilized within a test for the parameter; determining a color corresponding to the parameter, wherein the determining comprises accessing a color chemistry chart identifying colors corresponding to parameters; and generating, for the chemistry or instrument, an identifier for the chemistry or the instrument, wherein the identifier comprises an identification indicator of the color corresponding to the parameter.

A further embodiment provides a system for maintaining a color for a parameter across chemistries and instruments that are used in tests for the parameter, the system comprising: a plurality of chemistries, each of the chemistries being used within a test for a parameter; a plurality of instruments, each of the instruments being used within a test for a parameter; and a color chemistry chart, wherein the color chemistry chart identifies colors corresponding to parameters; wherein each of the chemistries and each of the plurality of instruments comprise a color identifier of the color corresponding to the parameter of the test of the chemistry or the instrument as identified from the color chemistry chart.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 2 illustrates an example color chemistry chart.

DETAILED DESCRIPTION

Figure 1:
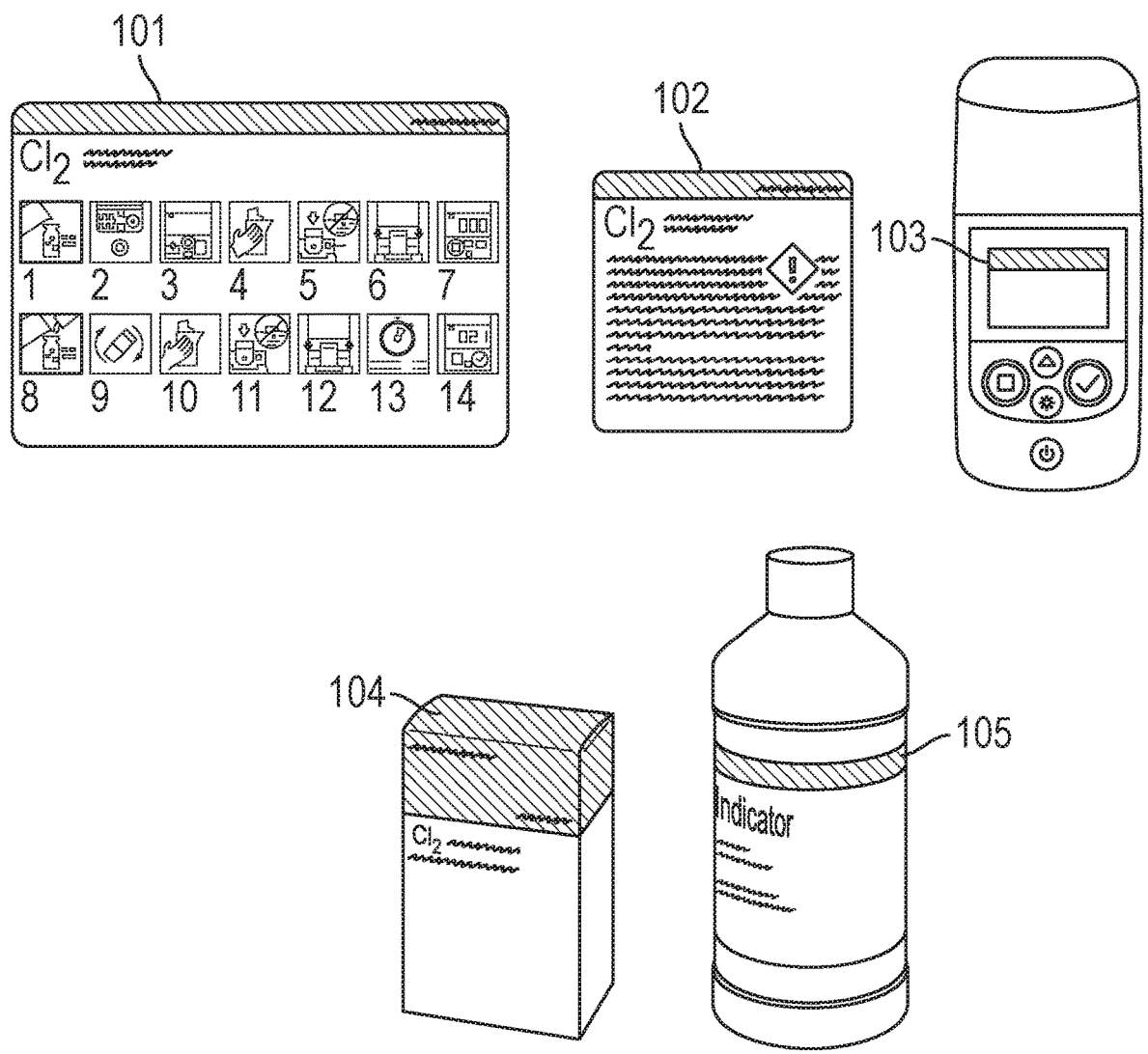
FIG. 1 illustrates example color identifiers based upon the chemistry or instrument type.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

For a person who tests, for example, an aqueous sample for different parameters, and, therefore, utilizes many different chemistries and/or instruments, it may be difficult to ensure that the correct chemistry and/or instrument is on hand at the time a test is needed. Additionally, since many chemistries and/or instruments are packaged similarly or look similar, it can be very easy to grab the wrong chemistry and/or instrument. In the case that the person does not realize they have the wrong chemistry and/or instrument before performing the test, this inability to easily distinguish chemistries and/or instruments can result in wasted chemistries and wasted time to perform the incorrect test. In some cases a person has to stock a vehicle or bag with the correct chemistries and/or instruments before traveling to a different location to perform the tests. For example, if the person is testing a pond or stream, the person has to take the chemistries and instruments needed to perform the test to the pond or stream. If the person has not gotten the correct chemistries and instruments packed, then the person may have to go back to the location to get the correct chemistry and then again travel to the testing location, which again can result in large expenditures of wasted time.

Conventionally, the chemistries and/or instruments have labels or other identifiers that identify what parameters the chemistry and/or instrument can be used to test for. However, these labels typically look the same and require the person to read the label in order to identify the parameter. Since some parameters have very similar names, for example, nitrate and nitrite, the person can easily misread the identifier and think the chemistry and/or parameter tests for something that it does not actually test for. Additionally, frequently chemistries and/or instruments are stocked together based upon parameter. For example, all chemistries that are used to test for iron would be stored in the same bin or on the same hanger. Thus, if someone accidentally puts the wrong chemistry in the incorrect storage location, a person may pick it up without really looking at the packaging or identifier and think it is the one they need simply based upon the storage location. Some identifiers include colors that help distinguish the parameter. However, these colors are not consistent. In other words, not all chemistries and/or instruments that are utilized in tests for the parameter have the same color identifier.

Accordingly, an embodiment provides a system and method for associating colors with parameters and maintaining a consistency in colors across the different chemistries and instruments that are used in tests for that parameter. The colors are then included in identifiers that are utilized on the packaging, labels, tags, or the like, for the chemistries and/or instruments. In some cases, the color corresponding to a particular parameter is based upon a color that is seen during the test. For example, when testing for chlorine a water sample may turn red after an indicator is added. Therefore, the identifier color that is selected for use with the chlorine parameter may be red. In the case that a particular identifier color has already been used for a different parameter, then a different identifier color is selected to correspond to the parameter. In selecting the different identifier color, the system makes sure that the difference in visual perceptibility between the colors, known in the industry as delta E or $\Delta E$, is above a predetermined threshold so that the colors can be easily distinguished by a person at a glance. Once an identifier color has been selected for a parameter, the color is utilized on the labels, tags, packaging, or other identifier for chemistries and instruments that are used in tests for the parameter across all products and product lines within a particular company or industry. Thus, the system assists in solving the problem of grabbing the wrong chemistry and/or instrument for a particular parameter because the chemistries and instruments have identifiers that allow for quick and easy identification of what parameter the chemistry and/or instrument is used to test for.

The illustrated example embodiments will be best understood by reference to the figures. The following description is intended only by way of example, and simply illustrates certain example embodiments.

To maintain consistent colors for parameters across products and throughout a company, a system may be used for associating different colors with different parameters. These colors corresponding to parameters can then be placed on labels, tags, packaging, on a display screen, or the like, for different chemistries and/or instruments that may be utilized in tests for the particular parameter. It should be noted that the colors correspond to the parameter that is being tested for and not the particular test that is utilized. In other words, there may be multiple tests that can be used to test for one particular parameter. Each of these tests would have the same color because they are used to test for the same parameter, even though the test is a different type of test.

FIG. 1 illustrates some examples of identifiers (e.g., labels, tags, packaging, display screens, etc.) that may be utilized. For example, an instruction sheet or test procedure 101 for a particular test may include a color bar across the top of a page. As another example, packaging for powder pillows 102 may include a label that has a color bar. As another example, a device used for testing 103 may include a color bar across the display screen. As another example, chemkey packaging 104 may include a colored section. As a final example, a reagent bottle label 105 may include a color bar. All of these are merely examples and not intended to be limiting as other methods and identifiers may be utilized to show the color corresponding to the parameter of the test. For example, a device may include a tape strip of the color. As another example, the packaging may include a color sticker that is separate from the label. Thus, numerous other techniques for including the parameter color on packaging, instruments, test procedures, and other materials used in testing are possible and contemplated. For ease of readability, the document will refer to the packaging. However, it should be understood that this term is intended to encompass chemistry packaging, device packaging or shells, documents, or any other material that may be utilized within a test for a parameter. The illustrated examples are devices, packaging, and materials associated with and owned by HACH® Company. HACH is a registered trademark of Hach Company in the United States and other countries.

As a starting point to determine what color should be included on the identifier, the system may first determine if the test results in a particular color when an indicator is used with the target analyte or parameter. In other words, the parameter may be associated with a particular color. For example, during the performance of the test or upon completion of the test, a particular color may be seen by a tester. As an example, during a test for chlorine the sample being tested may turn red. Parameters refers to the element being tested for and can be one of many different elements or parameters. Some example parameters include chlorine, lead, iron, nitrate, total organic carbon, ammonia, alkalinity, and pH. This list is merely illustrative to provide an idea of the different types of parameters. However, this list of parameters is not exhaustive. Some other possible parameters can be seen in FIG. 2. However, that listing is also not exhaustive.

If the color seen during the performance of the test has not previously been associated as an identifier color with a different parameter in the system, this color may then be assigned to the parameter. In other words, since many parameters result in similar colors being seen, commonly red, green, and blue, not all of the parameters can have the same associated packaging color. If the color has already been utilized for another parameter, a different color will be selected for that parameter. In choosing this different color it is important to ensure that the visual perceptibility between colors, referred to in the industry as delta E or ΔE, is above a predetermined threshold so that the parameter colors can be distinguished at a glance. Accordingly, in selecting the color the system may ensure that the delta E is greater than 10 between any two identifier colors. Since there is some variation in how delta E is measured by different systems or people within the industry, this value is not a hard value. Rather, this value is used as a starting point. Additionally, some colors having lower delta E values may offer enough of a contrast as compared to other colors, that they can be used for parameters. Thus, in selecting the color the system may identify a color for the parameter that has a measure of change in visual perception between the identified color and previously assigned colors meeting or exceeding a measure threshold. This measure threshold may ultimately be determined by a human selector based upon his/her own visual perception.

Once colors are assigned to all of the parameters, or the parameters that are most utilized by the company or industry, these colors may be utilized across the industry or company for all chemistries, instruments, documents, and the like, that are used in tests for the parameter. To ensure compliance with this color selection, a color chemistry chart may be created that identifies the parameter, includes a color bar for the parameter, a color code for the color associated with the parameter, and the like. An example color chemistry chart is shown in FIG. 2. The color code numbers shown in FIG. 2 are Pantone number values. However, other color values may be included or used. For example, the color values may include Red-Green-Blue (RGB) values, Cyan-Magenta-Yellow-Black (CMYK) values, or the like. In other words, any color values may be used or illustrated and which color value is used may be based upon the company or application. For example, RGB values may be utilized on displays, while Pantone values may be utilized on labels. In this case, a single value would be selected, for example, the Pantone value, and then converted to the other value, for example, the RGB value, in order to ensure consistency across the different packaging.

Figure 3:
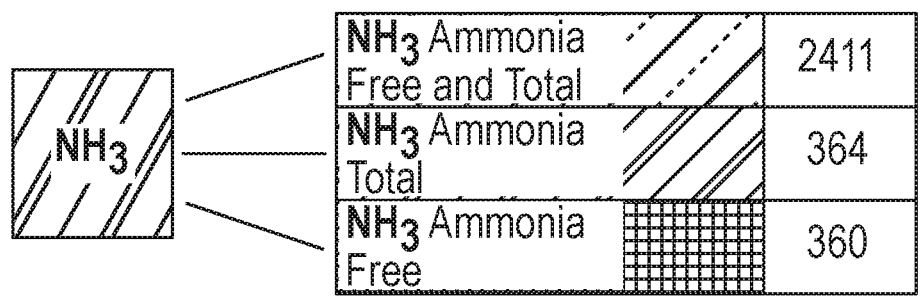
FIG. 3 illustrates an example color selection for measuring different values of the same parameter.

For color selection of parameters that allow for measurement of different values of the parameter, the identifier colors may be different tints or shades of the same color. FIG. 3 illustrates an example of different tints or shades for different measurements of the same parameter. In this example, the darker tint or shade of green is correlated to the largest measurement value which is a measurement of both total and free ammonia. A lighter tint or shade of green is then used for the next largest measurement value which is a measurement of just total ammonia. The lightest tint or shade of green is then used for the smallest measurement value which is a measurement of just free ammonia. By changing the tint or shade of the color for different measurement values of the same parameter, a user can easily identify which test objects should be used to produce the desired measurement.

Figure 4:
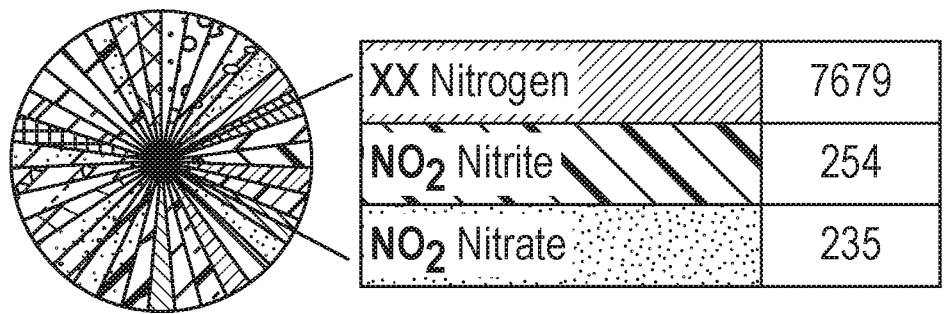
FIG. 4 illustrates an example color selection for similar parameters.

For parameters that are chemically similar to, close to, or related to other parameters, the selected color may be a different hue of the similar parameter. FIG. 4 illustrates an example of different hues of the same color for similar parameters. In this example, the similar parameters are nitrogen, nitrate, and nitrite. By keeping the colors for similar parameters as different hues, a user can easily identify, by packaging, test objects that are utilized in related test.

Since there are only so many colors that can be chosen from and that would offer enough noticeable visual distinction, colors may only be selected for the most commonly used parameters or the parameters that provide the largest market share. Thus, for tests of other parameters that do not meet the criteria for having a unique color, a generic color may be utilized. For example, for low volume parameters or parameters having a use volume of less than a predetermined value, one of plurality of generic colors may be selected for use in the identifier. The generic color may be one of a plurality of generic colors. For example, a company may utilize one generic color for chemistries and another generic color for hardware. Thus, a chemistry for a parameter would include an identifier having a color indication or identifier of the generic chemistry color.

In some cases, a chemistry or instrument, or supporting test documentation, may be utilized for more than one parameter. In such a case, one of the generic colors may be employed for use with the identifier. For example, if a chemistry can be used for two or more non-similar parameter tests, a generic color may be selected. As another example, if an instrument can be used for many different parameter tests, a generic color may be selected. On the other hand, if the parameters are similar or less than a predetermined number, the identifier may be generated to show all the different parameter colors. For example, if the chemistry can be used for two different parameters, the identifier may include two color bars, each representing a different parameter. As another example, if test documentation can be used for two different parameters, the identifier may be a repeating striping of the two colors that correspond to the parameters.

To designate which parameters an instrument, chemistry, test document, or the like can be used for, an identifier (e.g., label, color tag, display screen setting, tape color, packaging portion, etc.) may be generated. The identifier may include an identification indicator of the color that corresponds to the parameter of the test. The identification indicator may include a color bar, packaging portion, color strip, or any other visual indicator that includes the color. In the case of multiple parameters, the generated identifier may include different colors, with each color representing at least one of the test parameters. In the case of a low volume parameter or multiple parameters that have a generic color, the generated identifier may include one of the generic colors, which may be based upon the application (e.g., hardware, chemistry, documentation, etc.).

Thus, the described system and method allows for a user to easily distinguish between different chemistries, instruments, or other tests objects that are used for the testing of parameters. Such a system allows a user to more quickly and accurately identify what test object should be utilized for a particular test, thereby resulting in less waste of test objects due to incorrect testing and less wasted time due to having to retest or obtain the correct test object.

Figure 5:
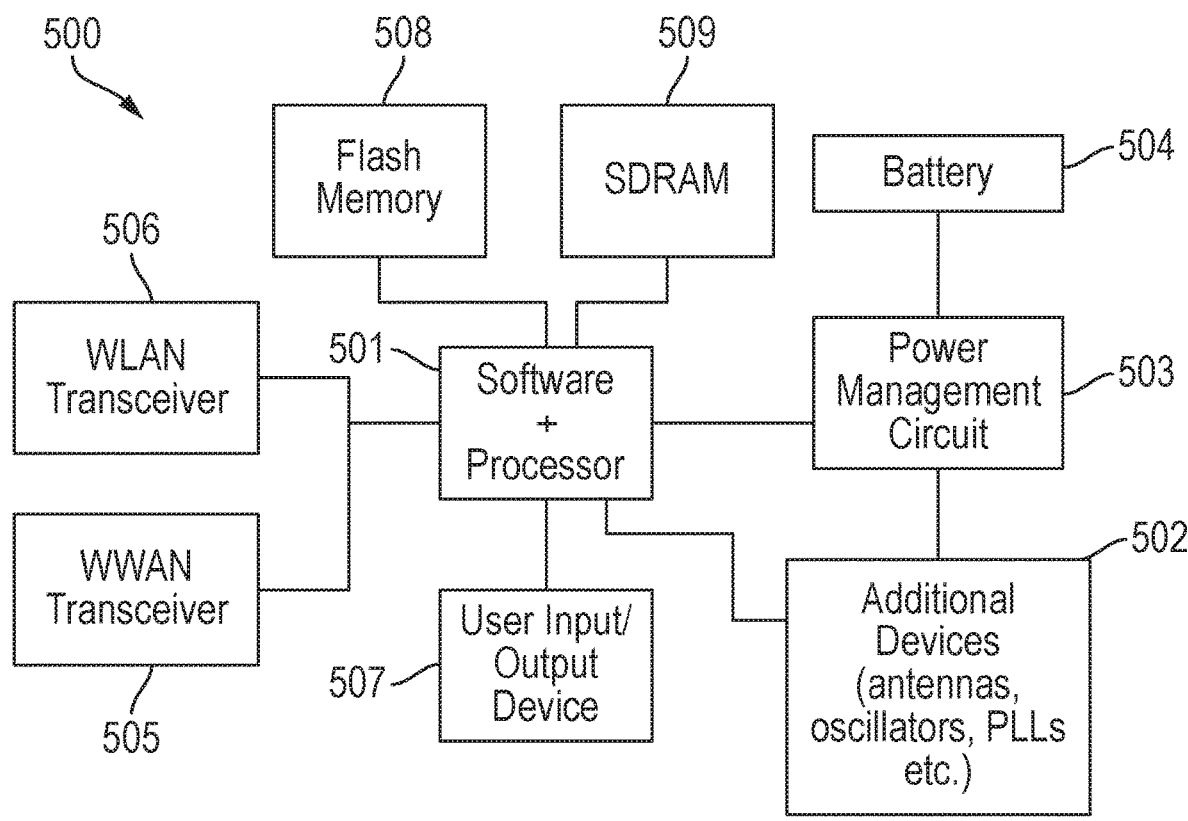
FIG. 5 illustrates an example of computer circuitry.

While various other circuits, circuitry or components may be utilized in information handling devices, with regard to an instrument for measuring fluid level and velocity according to any one of the various embodiments described herein, an example is illustrated in FIG. 5. Device circuitry 500 may include a measurement system on a chip design found, for example, a particular computing platform (e.g., mobile computing, desktop computing, etc.) Software and processor (s) are combined in a single chip 501. Processors comprise internal arithmetic units, registers, cache memory, busses, I/O ports, etc., as is well known in the art. Internal busses and the like depend on different vendors, but essentially all the peripheral devices (502) may attach to a single chip 501. The circuitry 500 combines the processor, memory control, and I/O controller hub all into a single chip. Common interfaces may include SPI, I2C and SDIO.

There are power management chip(s) 503, e.g., a battery management unit, BMU, which manage power as supplied, for example, via a rechargeable battery 504, which may be recharged by a connection to a power source (not shown). In at least one de sign, a single chip, such as 501, is used to supply BIOS like functionality and DRAM memory.

System 500 typically includes one or more of a WWAN transceiver 505 and a WLAN transceiver 506 for connecting to various networks, such as telecommunications networks and wireless Internet devices, e.g., access points. Additionally, devices 502 are commonly included, e.g., an a transmit and receive antenna, oscillators, PLLs, etc. System 500 includes input/output devices 507 for data input and display/rendering (e.g., a computing location located away from the single beam system that is easily accessible by a user). System 500 also typically includes various memory devices, for example flash memory 508 and SDRAM 509.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as an instrument, system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for selecting a color for a chemistry or instrument based upon a parameter of a test, the method comprising:
    identifying, using a processor within a system, a color corresponding to a parameter of a test for the parameter;
    selecting, by the system when the color corresponding to the parameter has not previously been used for another parameter, the color for designating a chemistry or an instrument as corresponding to the parameter;
    selecting, by the system when the color corresponding to the parameter has previously been used for another parameter, a different color other than the color for designating a chemistry or an instrument as corresponding to the parameter, wherein the selecting a color other than the color comprises identifying a different color against other previously selected colors a predetermined value from the other previously selected colors;
    utilizing the selected colors for parameters across tests objects that are utilized in tests for the parameters, wherein the test objects comprise chemistries and instruments, wherein the selected colors identify, on the test objects and to a user, at least one test object that tests for the parameter; and
    wherein selecting the color comprises selecting a hue, tint, or shade of the color for the parameter that is based upon a measurement value of the parameter.

2. The method of claim 1, wherein the measurement value of the parameter is correlated to a state of the parameter in the test.

3. The method of claim 1, wherein the parameters comprise a chemical component of the test.

4. The method of claim 1, wherein the measure of change in visual perception of the different color against other previously selected colors is greater than a delta E of 10.

5. The method of claim 1 wherein the selecting further comprises selecting one of a plurality of primary colors for the low volume parameters, the low volume parameters comprising parameters having a usage volume less than a predetermined volume.

6. The method of claim 1, comprising, selecting, for a chemistry or instrument utilized for testing more than one parameter, one of a plurality of primary colors, wherein the more than one parameter comprise non similar parameters each of a different type.

* * * * *